US006653467B1

(12) United States Patent
Matsuo et al.

(10) Patent No.: US 6,653,467 B1
(45) Date of Patent: Nov. 25, 2003

(54) MEDICAMENT FOR TREATMENT OF DUCHENNE MUSCULAR DYSTROPHY

(75) Inventors: Masafumi Matsuo, 3-31, Kitaochiai 5-chome, Suma-ku, Kobe-shi, Hyogo 654-0151 (JP); Yasuhiro Takeshima, Kobe (JP)

(73) Assignees: JCR Pharmaceutical Co., Ltd., Hyogo (JP); Masafumi Matsuo, Hyogo (JP)

(*) Notice: Subject to any disclaimer, the term of this patent is extended or adjusted under 35 U.S.C. 154(b) by 207 days.

(21) Appl. No.: 09/667,327

(22) Filed: Sep. 22, 2000

(30) Foreign Application Priority Data

Apr. 26, 2000 (JP) ......................................... 2000-125448

(51) Int. Cl.[7] ............................. C07H 21/04; C12Q 1/68

(52) U.S. Cl. .................. 536/24.5; 536/24.3; 536/24.31; 536/24.33; 435/6

(58) Field of Search ......................... 435/6, 91.1, 91.3, 435/325, 375; 536/23.1, 23.2, 24.3, 24.31, 24.33, 24.5; 514/44

(56) References Cited

U.S. PATENT DOCUMENTS

| | | |
|---|---|---|
| 5,151,510 A | 9/1992 | Stec et al. |
| 5,151,520 A | 9/1992 | Gottschalk et al. |
| 5,627,274 A | 5/1997 | Kole et al. |
| 5,665,593 A | 9/1997 | Kole et al. |
| 5,916,808 A | 6/1999 | Kole et al. |
| 5,948,680 A | 9/1999 | Baker et al. |
| 5,976,879 A | 11/1999 | Kole et al. |

FOREIGN PATENT DOCUMENTS

| | | |
|---|---|---|
| EP | 1 054 058 A1 * | 5/2000 |
| JP | 8-510130 | 10/1996 |
| JP | 2000125448 | 4/2000 |
| JP | 00325085 | 11/2000 |
| JP | 2000348957 | 12/2000 |
| WO | WO 89/06286 * | 12/1988 |
| WO | 94/26887 | 11/1994 |

OTHER PUBLICATIONS

T Ito et al., American Journal of Human Genetics, "Identification of a splicing enhancer sequence within exons of the dystrophin gene using a chimeric dsx pre–mRNA," Oct. 1999, vol. 65, No. 4, p. A188.*

K–Y Jen et al., Stem Cells, "Suppression of Gene Expression by Targeted Disruption of Messenger RNA: Available Options and Current Strategies," 2000, 18, pp. 307–319.*

DW Green et al., American College of Surgeons," Antisense Oligonucleotides:An Evolving Technology for the Modulation of Gene Expression in Human Disease," Jul. 2000, vol. 191, No. 1, pp. 93–105.*

AD Branch, TIBS, "A good antisense molecule is hard to find," Feb. 1998, pp. 45–50.*

S Agrawal et al.,Molecular Medicine Today, "Antisense therapeutics:is it as simple as complementary base recognition?"Feb. 2000, vol. 6, pp. 72–81.*

JCT van Deutekom et al., Human Molecular Genetics, "Antisense–induced exon skipping restores dystrophin expression in DMD patient derived muscle cells," 2001, vol. 10, No. 15, pp. 1547–1554.*

Askari et al., "Molecular Medicine Antisense–Oligonucleotide Therapy", *N. Engl. J. Med.*, vol. 334, pp. 316–318 (1996).

Trojan et al., "Treatment and Prevention of Rat Glioblastoma by Immunogenic C6 Cells Expressing Antisense Insulin–Like Growth Factor I RNA", *Science*, vol. 259, pp. 94–97 (1993).

Trojan et al., "Loss of Tumorigenicity of Rat Glioblastoma Directed by Episome–Based Antisense cDNA Transcription of Insulin–Like Growth Factor I", *Proc. Nat.. Acad. Sci. USA*, vol. 89, pp. 4874–4878 (1992).

Martin, "Early Clinical Trials with GEM 91, A Systemic Oligodeoxynucleotide", *Applied Antisense Oligonucleotide Technology*, pp. 387–393 (1998).

Dunckley et al., "Modification of Splicing in the Dystrophin Gene in Cultured Mdx Muscle Cells by Antisense Oligoribonucleotides", *Human Molecular Genetics*, vol. 5, No. 1, pp. 1083–1090 (1995).

Crooke, *Antisense Research and Application*, pp. 1–50 (1998).

Agarwal, "Antisense Oligonucleotides: Towards Clinical Trials", *TIBTECH*, pp. 376–387 (1996).

Branch, "A Good Antisense Molecule is Hard to Find", *TIBS 23*, pp. 45–50 (1998).

Koenig, M., et al., Cell, 50:509–517 (1987).

Roberts, R., et al., Genomics, 16:536–538 (1993).

Nishio, H., et al., J. Clin. Invest., 94:1037–1042 (1994).

Ahn, A. and Kunkel, L., Nature Genetics, 3:283–291 (1993).

D'Souza, V., et al., Human Mol. Genetics, 4:837–842 (1995).

Hoffman, E. and Kunkel, L., Neuron, 2:1019–1029 (1989).

Chamberlain, J., et al., Nucleic Acids Res., 16:11141–11156 (1988).

(List continued on next page.)

Primary Examiner—Karen Lacourciere
(74) Attorney, Agent, or Firm—Greenblum & Bernstein, P.L.C.

(57) ABSTRACT

Antisense oligonucleotides comprising a nucleotide sequence complementary to the nucleotide sequence of SEQ ID NO:1 or NO:2 are disclosed. The antisense oligonucleotides are used for treatment of specific types of Duchenne muscular dystrophy which is attributed to a change in number of the nucleotides composing one or more exons adjacent to exon 43 or 53, respectively, in human dystrophin mRNA, wherein the change is due to deletion of one or more nucleotides from the normal nucleotide sequence for the exons, wherein the net of the change in number of the nucleotides is expressed as a reduction of (3×N+1) nucleotides, wherein N is zero or a natural number.

2 Claims, No Drawings

OTHER PUBLICATIONS

Beggs, A., et al., Human Genetics, 86:45–48 (1990).
Bulfield, G., et al., Proc. Natl. Acad. Sci., 81:1189–1192 (1984).
Monaco, A., et al., Genomics, 2:90–95 (1988).
Morgan, J., Human Gene Ther., 5:165–173 (1994).
Nicholson, L., et al., J. Neurol. Sci., 94:137–146 (1989).
Klein, C., et al., Am. J. Human Genetics, 50:950–959 (1992).
Wilton, S., et al., Muscle Nerve, 20:728–734 (1997).
Sakuraba, H. Et al., Genomics, 12:643–650 (1992).
Matsuo, M., et al., Biochem. Biophys. Res. Commun., 170:963–967 (1990).
Matsuo, M., et al., J. Clin. Invest., 87:2127–2131 (1991).
Hagiwara, Y., et al., Am. J. Human Genetics, 54:53–61 (1994).
Matsuo, M., et al., Biochem. Biophys. Res. Commun., 182:495–500 (1992).
Dietz, H., et al., Science, 259:680–683 (1993).
Takeshima, Y., et al., J. Clin. Invest., 95:515–520 (1995).
Watakabe, A., et al., Genes Dev., 7:407–418 (1993).
Pramono, Z., et al., Biochem. Biophys. Res. Commun., 226:445–449 (1996).
Inoue, K., et al., Proc. Natl. Acad. Sci., 89:8092–8096 (1992).
Oligonucleotides and Analogues: A Practical Approach, F. Eckstein, Ed., 87–108, Oxford University Press, Oxford, England.

* cited by examiner

MEDICAMENT FOR TREATMENT OF DUCHENNE MUSCULAR DYSTROPHY

FIELD OF THE INVENTION

The present invention relates to medicaments for treatment of Duchenne muscular dystrophy, which medicaments are designed to correct an existing shift of the amino acid reading frame in dystrophin pre-mRNA by inducing in a predetermined manner an exon skipping in the pre-mRNA having the reading frame shift resulting from abnormalities in dystrophin gene. More specifically, the present invention relates to splicing enhancer sequences (SES's) in dystrophin gene which can be used for the preparation of medicaments for treatment of certain types of Duchenne muscular dystrophy, as well as to antisense oligonucleotides against the splicing enhancer sequences, and medicaments comprising thereof.

BACKGROUND OF THE INVENTION

Today, it has become possible to diagnose some hereditary diseases caused by abnormal splicing of corresponding pre-mRNA molecules. An intractable disease, muscular dystrophy, has come to draw particular attention. Muscular dystrophy is divided into Duchenne muscular dystrophy (DMD) and Becker muscular dystrophy (BMD). DMD is a hereditary muscular disease of highest incidence, occurring in one in 3,500 live male births. Patients of DMD at first exhibit lowered muscular power in their infancy, suffer from progressive muscular atrophy since then on, and eventually die in their age of around 20. No effective medicament is so far available for DMD, and development of a medicament for it has been longed for by the patients around the world. In 1987, dystrophin gene, which is the causative gene of DMD, was found using retrospective genetics, and BMD also was found to result from abnormality of the same dystrophin gene [Koenig, M. et al., Cell, 50:509–517 (1987)]. As for BMD, its onset is relatively late, observed in the adulthood, and nearly normal survival is allowed, although a mild loss of muscular power is observed after the onset of the disease.

Dystrophin gene is located in the subregion 21 of the short arm of the X-chromosome. The size of dystrophin gene is 3,0 Mb, the largest known human gene. Despite that large size, it is regions of only 14 kb in total of the dystrophin gene that encodes dystrophin protein, and the encoding regions are divided into no less than 79 exons which are distributed within the gene [Roberts, R G., et al., Genomics, 16:536–538(1993)]. Its pre-mRNA, the transcript of dystrophin gene, undergoes splicing into the mature mRNA of 14 kb. The gene includes eight distinct promoter regions, which are also distributed within the gene and responsible for production of respective distinct mRNAs [Nishio, H., et al., J. Clin. Invest., 94:1073–1042(1994), Ann, A H. and Kunkel, L M., Nature Genet., 3:283–291(1993), D'Souza, V N. et al., Hum. Mol. Genet., 4:837–842(1995)]. Thus, dystrophin gene and its transcript are very complex in structure.

Genetic diagnosis of DMD and BMD was performed in early days using fragments of dystrophin gene, and then by Southern blot analysis using cDNAs as probes. Thus, it was revealed that approximately six tenth of DMD/BMD patients have abnormalities such as large loss or multiplication in dystrophin gene [Hoffman, E P. and Kunkel, L M., Neuron, 2:1019–1029(1989)]. Most of the abnormalities found in the gene in DMD/BMD patients was a loss in the gene, with sizes of as big as several kb. As abnormalities in dystrophin gene detected by Southern blotting were concentrated on two "hot-spots" in the gene, multiplex PCR was designed for genetic diagnosis which, by focusing on 19 exons in those hot-spots, can easily identify a deletion using two PCR (polymerase chain reaction) systems [Chamberlain J S., et al., Nucleic Acids Res., 16:11141–11156(1988), Beggs A H., et al., Hum. Genet., 86:45–48(1990)]. Today, the multiplex PCR has become the most popular diagnosing method, for it quickly gives results and can detect 98% of gene abnormalities which are detectable by Southern blotting.

There is known an animal model for DMD, a mdx (X chromosome-linked muscular dystrophy) mouse [Bulfield, G. et al., Proc. Natl. Acad. Sci. U.S.A., 81:1189–1192 (1984)].

Due to a nonsense mutation within exon 23 of the mouse dystrophin, this gene in the mdx mouse is inactivated, i.e., translation is terminated within exon 23. No functional dystrophin is expressed in the mdx mouse, although a trace of dystrophin-positive muscle fiber is detected histochemically.

No explanation had been given to the cause of the great difference in pathological conditions clinically observed between the two diseases, DMD and BMD, both resulting from apparently similar abnormalities in the same dystrophin gene, until so-called frameshift hypothesis was proposed [Monaco, A P., et al., Genomics, 2:90–95(1988)]: In DMD, a partial deletion present in the gene results in a (out-of-frame) shift of amino acids reading frame along the dystrophin mRNA and an eventually emerging stop codon puts an end to the dystrophin synthesis halfway. In contrast, in BMD, the reading frame is kept intact (in-frame) in spite of a partial deletion present in the gene and dystrophin protein therefore is synthesized, though it differs size from wild dystrophin. In fact, analyses of dystrophin in patients' muscle demonstrated that dystrophin was lost in DMD, whereas it occurred in BMD, though with an altered staining property. In addition, according to comparisons made of the phenotypes DMD/BMD with the types of reading frames deduced from the abnormalities in dystrophin gene, the frameshift hypothesis has been proved proper in more than 90% of the patients.

Though not established as a method for treatment of muscular dystrophy, introduction of functional dystrophin gene has been attempted by means of myoblasts implantation or utilizing plasmids or viral vectors [Morgan, J., Hum. Gene. Ther. 5:165–173(1994)].

Dystrophin-positive muscle fibers are also found in many DMD patients (Nicholson, L. et al., J. Neurol. Sci., 94:137–146(1989)]. The dystrophin positive fibers found in DMD patients have been said to be produced through exon skipping [Klein, C. et al., Am. J. Hum. Genet., 50:950–959 (1992)]. In fact, an in-frame dystrophin transcript was identified which had underwent skipping of an exon containing a major nonsense mutation [Wilton, S. et al., Muscle Nerve, 20:728–734(1997)].

Genetic information transcribed from the gene undergoes splicing to remove introns and thus mature mRNA is produced, which exclusively consists of exons. The mature mRNA is then translated along its reading frame to synthesize a protein strictly in consistent with the genetic information encoded in the gene. In the splicing step of pre-mRNA, there is a mechanism for precisely distinguishing introns from exons in the nucleotide sequence of the pre-mRNA. For this purpose, sequences in intron-exon boundaries are conserved in every gene in certain rules, and thus known as consensus sequences.

Consensus sequences are known at three sites: a splice donor site at the 5' end of an intron (the site providing an exon-intron junction), a splice acceptor site at the 3' end of the intron, and a branch site.

It has been reported concerning a number of diseases that substitution of just a single nucleotide in one of these consensus sequences results in abnormal splicing. This indicates that the consensus sequences are the keys to splicing [Sakuraba, H. et al., *Genomics*, 12: 643–650 (1992)].

The present inventors for the first time in Japan performed a PCR diagnosis of dystrophin gene abnormalities in DMD/BMD patients, and thereby showed that there is no significant difference between Westerners and Japanese in the type of abnormalities in the gene, i.e., no significant racial difference exists. Though the gene abnormalities thus found by the genetic diagnosis were, without exception, gigantic ones involving several kb to several hundred kb nucleotides, further analyses for the first time led to successful identification of the nucleotide sequence of the deleted part of a dystrophin gene, and the result was reported along with the corresponding case named "dystrophin Kobe" [Matsuo, M, et al., *Biochem. Biophys. Res. Commun.*, 170:963–967 (1990)].

The case with the gene abnormality named "dystrophin Kobe" is a DMD case. The results of its multiplex PCR analyses revealed that no band corresponding to exon 19 was found at its expected position in amplified products of genomic DNA, apparently indicating loss of exon 19. However, in a reaction attempted to amplify the exon 19 region of the genomic DNA, exon 19, though smaller than its normal size, was detected as the amplification product, indicating that the disease was not brought about by a simple exon deletion which had been frequently observed in dystrophin gene. PCR amplification was performed on exon 19 region of dystrophin genes from the family members of the patient. The DNAs from his mother and younger sister gave, along with normal one, an amplification product of the same size as the patient's amplification product, indicating that the former two were carriers of this abnormal gene.

Then, sequencing of the abnormal amplification product obtained from the patient showed that 52 nucleotides were lost from exon 19 that is made up of 88 nucleotides. The loss of these 52 nucleotides from the exon sequence implies that a shift of the reading frame is resulted in the dystrophin mRNA (rendering it out-of-frame) and thus giving rise to a stop codon within exon 20. The result of the genetic diagnosis was consistent with the clinically given diagnosis of DMD.

To examine the effect of the lost part of exon 19 identified in dystrophin Kobe on splicing, dystrophin mRNA from the patient was analyzed [Matsuo, M., et al., *J. Clin. Invest.*, 87:2127–2131(1991)].

First, using mRNA from leukocytes of the patient and reverse transcriptase, cDNA was prepared, which then was amplified by nested-PCR. Amplification of a region covering from exon 18 through exon 20 gave an amplified fragment, which was smaller than the size expected from the identified abnormality in the genome. This suggested a possibility that either the mRNA had different type of abnormality from the abnormality in genomic DNA or there existed some difference between the mRNAs from leukocytes and the muscular cells. Then, in order to make sure that this mRNA abnormality is shared also by the mRNA from muscular cells associated with the disease, a region covering from exon 18 through exon 20 was amplified by PCR using as a template cDNA prepared from mRNA from the muscular cells. The product thus obtained was the same as the amplification product of the region covering exon 18 through exon 20 from leukocytes.

Then, sequencing of the thus obtained small-sized abnormal amplification product revealed that entire exon 19 sequence was lost from dystrophin cDNA of the dystrophin Kobe patient, with exon 18 directly connected to exon 20. This result was not in agreement with the fact that the genomic exon 19 sequence lacked just 52 nucleotides, with the other 36 nucleotides remaining in place. This indicates that in dystrophin Kobe, an exon skipping took place in the maturation process of pre-mRNA by splicing out of the 36 nucleotides remaining in exon 19.

Not a small number of cases have been reported in which exon skipping occurs as a result of abnormality of a gene. It was reported for the first time by the present inventors that a point mutation in dystrophin gene caused an exon skipping [Hagiwara, Y., *Am. J. Hum. Genet.*, 54:53–61(1994)]. All of these mutations of the gene causing exon skipping were those localized in consensus sequences, which determine the splicing sites as aforementioned.

In contrast, in dystrophin Kobe found by the present inventors, no abnormality was detected in consensus sequences, with 52 nucleotides found deleted just from "within" the exon. The reason of the exon skipping in the case, therefore, was unknown.

As the exon skipping found in dystrophin Kobe was not attributable to an abnormality in the primary structure of its DNA or pre-mRNA, the cause of the exon slipping was expected to reside in an abnormality in the secondary structure of its pre-mRNA. Thus, its secondary structure was analyzed. Analysis was done on computer using an algorithm by Zuker et al. designed for calculation of the secondary structure with the most energetically stable bonding of bases [Matsuo, M. et al., *Biochem. Biophys. Res. Commun.*, 182:495–500(1992)]. According to an analysis of the 617 bases including nucleotide sequences of wild-type dystrophin exon 19 and the introns on both sides, the pre-mRNA was shown to have a relatively simple stem-loop structure. A characteristic intra-exon hairpin structure was noted, in which base pairs were made within the exon 19 sequence itself. In contrast, deduction of the secondary structure of pre-mRNA from a sequence consisting of the dystrophin Kobe's exon with the 52-base intra-exon deletion and adjacent introns gave a result greatly different from that obtained from the wild type. The most notable feature with regard to dystrophin Kobe was that it had a simple stem structure in which the exon sequence made pairs only with an intron sequence. This result suggested that the intra-exon hairpin structure found in the wild type might be the factor characterizing the structure of the dystrophin exon.

Then, 22 exons for which the sequence of respective adjacent introns were known were chosen out of the 79 exons of dystrophin gene, and the secondary structures of their pre-mRNA were analyzed. The results showed that all the exons analyzed had an intra-exon hairpin structure. Thus, the presence of an intra-exon hairpin structure was thought to be an essential element for the exon to function. These findings strongly suggested that the exon skipping found in dystrophin Kobe occurred due to the elimination of the intra-exon hairpin structure in its pre-mRNA. Also suggested was that some exon sequence itself played an important role in the recognition of exon during splicing.

Recently, it was reported that, in addition to an abnormality in the consensus sequences, an abnormal sequence within an exon could also cause exon skipping [Dietz, H C., et al., *Science*, 259:680–683(1993)]. Thus, attention has been drawn not only to the consensus sequences but also to sequences within exons as factors serving to decide splicing sites. These have thrown over the so-far conventional concept of splicing in molecular biology.

As it was suggested that a sequence within exon 19 would be important in determining the splicing site, an in vitro splicing system was constructed and a test carried out to confirm it [Takeshima, Y., et al., *J. Clin. Invest.*, 95:515–520 (1995), Japanese Patent Application No. H11-140930]. First, a mini-gene was created consisting of exons 18 and 19 plus intron 18 of dystrophin gene. A radioisotope-labeled pre-mRNA was synthesized based on the mini-gene. The pre-mRNA thus obtained was mixed with HeLa cell nucleus extract and splicing was allowed to proceed in vitro. Thus produced mature mRNA was separated by electrophoresis. In this reaction system, splicing occurred as normal with pre-mRNA having normal exon 19, giving rise to a mature mRNA in which exons 18 and 19 were directly connected. When the exon 19 sequence was replaced with that of dystrophin, however, mature mRNA was not obtained. This indicated that the 52 nucleotide lost from exon 19 in dystrophin Kobe had an important role in splicing.

This abnormal splicing, however, might have been due to the "size" of exon 19 which was shortened to 36 nucleotides. Thus, an experiment was carried out in the same manner after insertion of the deleted sequence of exon 19 of dystrophin Kobe in the opposite orientation for making up for the loss. With this pre-mRNA, splicing took place, but with a low efficiency. This result indicated that splicing efficiency is lowered with an abnormal intra-exon sequence even if the length of such exon is normal, and further indicated that it is the nucleotide sequence in the exon (not its size) that is important.

Then, in order to examine the effect of intra-exon nucleotide sequences on splicing, pre-mRNAs were synthesized containing one of two different sequences inserted for the lost 52 nucleotides and their efficiency of splicing was examined. With two pre-mRNAs containing an inserted fragment of β-globin gene or ampicillin resistance gene, splicing was observed but with a very low efficiency. The β-globin gene insertion, however, resulted in relatively high splicing efficiency when compared with the insertion of the ampicillin resistance gene. The former nucleotide sequence was rich in purine bases. A purine-dominated sequence within an exon is thought to take part in exon recognition [Watanabe, A., et al., *Genes Dev.*, 7:407–418(1993)].

These results of experiments demonstrated that not only a consensus sequence but also a sequence within the downstream exon is involved in splicing and introduced new concept into processing of genetic information.

<Regulation of Splicing with Antisense Oligonucleotide>

Based on the above finding that a sequence within exon 19 of dystrophin gene is highly important for its splicing to take place, the inventors continued the study focusing on the possibility that abnormal splicing could be induced artificially by breaking the sequence. Thus, an 2'-O-methyl oligoRNA was synthesized which was complementary to the 31-nucleotide sequence set forth under SEQ ID NO:6 in the Sequence Listing that included the nucleotide sequence set forth under SEQ ID NO:5 in the Sequence Listing, which were part of the 52-nucleotide sequence lost in dystrophin Kobe. Using the aforementioned in vitro splicing system, assessment was made on the effect of this oligoRNA on splicing of pre-mRNA consisting of [exon 18]-[intron 18]-[exon 19]. The results showed an inhibition of the splicing reaction, which inhibition was dependent on the amount of added antisense oligonucleotide and the duration of the reaction. Thus, it was for the first time proved experimentally that splicing at an intron of dystrophin can be inhibited by an antisense oligonucleotide. This then suggested that splicing reaction occurring in the nucleus could be artificially manipulated [Takeshima, Y. et al., *J. Clin. Invest.*, 95:515–520(1995)].

<Regulation of Splicing Within the Nucleus>

To examine whether it is also possible within the nucleus of living cells to regulate splicing of dystrophin pre-mRNA with the antisense oligonucleotide, the present inventors introduced into human normal lymphoblastoid cells an antisense oligoDNA having a nucleotide sequence complementary to the nucleotide sequence set forth under SEQ ID NO:6 in the Sequence Listing that included the nucleotide sequence set forth under SEQ ID NO:5, and then analyzed the dystrophin mature mRNA thus produced in the presence of the antisense oligoDNA [Zacharias A. D P. et al., B. B. R. C., 226:445–449(1996)]. Briefly, introduction of the antisense oligoDNA into the nucleus was conducted by mixing it with LipofectAMINE and adding the mixture to the culture medium of the lymphoblastoid cells. As a result it was found that, despite the previous results obtained with the in vitro splicing system, skipping of exon 19 was induced in the human lymphoblastoid cells by the antisense oligoDNA against the nucleotide sequence of dystrophin exon 19, thus giving rise to a mRNA in which exon 18 is connected directly to exon 20. Extended duration of culture led to a complete induction of this exon skipping, thus exclusively providing a mRNA from which exon 19 was deleted. It was further confirmed that splicing process with regard to the other exons was not affected by the antisense oligoDNA.

Up to now, antisense oligonucleotides (AOs) have been applied to regulate gene expression for inhibition of protein translation. AOs have also been used to attack a specific region in a DNA to inhibit its transcription by RNA polymerase II. Another approach has also been known in which an abnormal splicing of pre-mRNA is inhibited using an antisense oligonucleotide [Japanese Laid-open Patent Publication No. H8-510130]. As it does not induce ribonuclease H activity, phosphorothioate-2'-O-methyloligonucleotide has been used to block a shifted splicing site in the pre-mRNA in patients of thalasemia-based anemia to restore proper splicing.

<Therapeutic Application of Artificially Induced Exon Skipping>

As noted above, DMD results from an abnormality which causes a shift of the amino acids reading frame of dystrophin mRNA to render it out-of-frame. Should this abnormal reading frame be changed to an in-frame arrangement, then DMD would be converted to BMD, and therefore amelioration of the symptoms would be expected. Assuming a patient with a simple loss of exon 20, for example, his phenotype will be of DMD, for the simple loss of exon 20, which consists of 242 nucleotides, naturally will cause a frameshift and thereby allowing a stop codon to emerge halfway in the process of translation, thus leading to the cessation of dystrophin synthesis halfway. However, if exon 19 skipping could be artificially induced by administering to the patient an antisense oligonucleotide against exon 19 such as the one used in the aforementioned experiment, the reading frame could turn in-frame again because of the total loss of 330 nucleotides from the pre-mRNA due to the loss of 242 nucleotides of exon 20 plus 88 nucleotides of exon 19. Therefore, DMD could, at least theoretically, be converted to BMD.

As mentioned above, however, dystrophin gene is structurally very complex and its pre-mRNA, too, takes a complex secondary structure including a number of large introns to be spliced out, which secondary structure regulates the normal procession of splicing. Therefore, practical applicability was unpredictable as to; whether skipping of exon 19 could be induced as desired by an antisense oligonucleotide against exon 19 in myoblasts from a patient with simple deletion of exon 20 as well as in normal human lymphoblastoid cells; whether, assuming that exon 19 skipping successfully was induced, a shift of the mRNA reading frame, from out-of-frame to in-frame position, could take place without affecting the splicing-out of exon 20 or splicing at other sites in the pre-mRNA which already had an abnormality leading to splicing out of exon 20; or whether, assuming the in-frame conversion was achieved, thus produced mRNA could function to efficiently produce a dystrophin-like protein.

Upon this background, one of the present inventors demonstrated that splicing out of exon 19 can be induced with an antisense oligonucleotide against exon 19 in the cells of a DMD patient having complete loss of exon 20 in mature dystrophin mRNA, and that the existing shift of the reading frame along the mature dystrophin mRNA can thereby be corrected, thus converting the dystrophin-negative cells to positive ones. Based on the results, an agent for treatment of DMD has been disclosed [Japanese Patent Application No. 11–140930].

It was thus demonstrated that an antisense oligonucleotide against dystrophin exon 19, when added to the culture medium of myoblasts of a DMD patient having a simple loss of exon 20, was incorporated into the myoblasts and then into the nucleus, and led to restoration of the reading frame, which now turned back to the in-frame position from the former out-of-frame position although having entire loss of exon 19 and 20, thus producing a dystrophin of full length except for the deleted part encoded by exons 19 and 20. This result strongly suggest the possibility that, by administering an antisense oligonucleotide against exon 19 to a DMD patient having a simple loss of exon 20, the very serious case of DMD can be converted to a milder one of BMD.

Thus, in addition to the so-far known consensus sequences present exon-intron boundaries, a splicing enhancer sequence (SES) present within an exon plays an important role in determining the site of splicing when a pre-mRNA transcribed from the genome is spliced into a mature mRNA. As aforementioned, one of the present inventors identified an SES in exon 19 and further demonstrated that an antisense oligonucleotide against the SES can induce skipping of exon 19.

Thus, by correcting the existing shift of reading frame by induction of exon skipping in the process of splicing of dystrophin pre-mRNA, it is possible to convert DMD to BMD in which a dystrophin protein with partly restored function is produced. However, a variety of mutation sites leading to DMD are thought to exist in dystrophin gene. Therefore, for providing therapy for such a variety of mutation sites, it is important to identify not only the SES in exon 19 but also other SES's located at or near the sites with high incidence of mutation in dystrophin gene. Thus, the objective of the present invention is to find novel SES's within dystrophin exons and provide thereupon new medicaments for treatment of DMD.

SUMMARY OF THE INVENTION

Upon the above background, the present inventors successfully identified new SES's within exons 43 and 53, respectively, of dystrophin gene, and thereupon created new means for treatment of Duchenne muscular dystrophy.

Thus the present invention provides an oligonucleotide selected from the group consisting of an RNA having the nucleotide sequence set forth under SEQ ID NO:1 or NO:2 in the Sequence Listing and a DNA having a nucleotide sequence complementary to a complementary sequence to said nucleotide sequence set forth under SEQ ID NO:1 or NO:2 in the Sequence Listing. Of these oligonucleotides, the RNAs correspond to the SES (set forth under SEQ ID NO:1 in the Sequence Listing) within exon 43 and the SES (set forth under SEQ ID NO:2 in the Sequence Listing) within exon 53, respectively, of human dystrophin pre-mRNA. These RNAs and DNAs are used as templates for production of antisense nucleotides as therapeutic agents for Duchenne muscular dystrophy discussed below.

The present invention further provides antisense oligonucleotides comprising nucleotide sequences complementary to the nucleotide sequences set forth under SEQ ID NO:1 or 2 in the Sequence Listing.

The antisense oligonucleotides, when administered, can induce skipping of exon 43 or 53 in the splicing process of human dystrophin mRNA as they are complementary to the SES (set forth in the form of an equivalent DNA under SEQ ID NO:1) within exon 43 or the SES (set forth in the form of an equivalent DNA under SEQ ID NO:2) within exon 53, respectively, of human dystrophin mRNA. Therefore, these antisense oligonucleotides can be used as therapeutic agents against particular types of Duchenne muscular dystrophy based on correcting the shift of reading frame.

The above antisense oligonucleotides may be DNAs having the nucleotide sequences set forth under SEQ ID NO:3 and NO:4, respectively, in the Sequence Listing and may also be phosphorothioate DNAs having the same nucleotide sequences as them. The sequences are complementary to sequences which include the SES and adjacent nucleotide sequences at both ends thereof within exon 43 and 53, respectively. A DNA comprising one of these sequences can therefore more strongly hybridize with the SES within exon 43 or 53, respectively, and block their functions.

The present invention further provides use of the antisense oligonucleotide having a nucleotide sequence complementary to the nucleotide sequence set forth under SEQ ID NO:1 in the Sequence Listing for the manufacture of a medicament for treatment of Duchenne muscular dystrophy which is attributed to a change in number of the nucleotides composing one or more exons adjacent to exon 43 in human dystrophin mRNA, wherein said change is due to deletion of one or more nucleotides from the normal nucleotide sequence for said exons, wherein the net of said change in number of the nucleotides is expressed as a reduction of $(3 \times N+1)$ nucleotides, wherein N is zero or a natural number. The antisense oligonucleotide may be a DNA selected from the group consisting of the DNA having the nucleotide sequence set forth under SEQ ID NO:3 in the Sequence Listing and a phosphorothioate DNA having the same nucleotide sequence as the nucleotide sequence set forth under SEQ ID NO:3.

The present invention further provides a medicament for treatment of Duchenne muscular dystrophy which is attributed to a change in number of the nucleotides composing one or more exons adjacent to exon 43 in human dystrophin mRNA, wherein said change is due to deletion of one or more nucleotides from the normal nucleotide sequence for said exons, wherein the net of said change in number of the nucleotides is expressed as a reduction of $(3 \times N+1)$ nucleotides, wherein N is zero or a natural number, said medicament comprises one of the above antisense oligonucleotides against the SES within exon 43, in a pharmaceutically acceptable injectable medium.

The present invention further provides use of the antisense oligonucleotide having a nucleotide sequence complementary to the nucleotide sequence set forth under SEQ ID NO:2 in the Sequence Listing for the manufacture of a medicament for treatment of Duchenne muscular dystrophy which is attributed to a change in number of the nucleotides composing one or more exons adjacent to exon 53 in human dystrophin mRNA, wherein said change is due to deletion of one or more nucleotides from the normal nucleotide sequence for said exons, wherein the net of said change in number of the nucleotides is expressed as a reduction of (3×N+1) nucleotides, wherein N is zero or a natural number. The antisense oligonucleotide may be a DNA selected from the group consisting of the DNA having the nucleotide sequence set forth under SEQ ID NO:4 in the Sequence Listing and a phosphorothioate DNA having the same nucleotide sequence as the nucleotide sequence set forth under SEQ ID NO:4.

The present invention further provides a medicament for treatment of Duchenne muscular dystrophy which is attributed to a change in number of the nucleotides composing one or more exons adjacent to exon 53 in human dystrophin mRNA, wherein said change is due to deletion of one or more nucleotides from the normal nucleotide sequence for said exons, wherein the net of said change in number of the nucleotides is expressed as a reduction of (3×N+1) nucleotides, wherein N is zero or a natural number, said medicament comprises one of the above antisense oligonucleotides against the SES within exon 53, in a pharmaceutically acceptable injectable medium.

Furthermore, the present invention provides a method of treatment of a human patient of Duchenne muscular dystrophy comprising administering to said patient an therapeutically effective amount of an antisense oligonucleotide comprising a nucleotide sequence complementary to the nucleotide sequence set forth under SEQ ID NO:1 or NO:2 in the Sequence Listing, wherein said Duchenne muscular dystrophy is attributed to a change in number of the nucleotides composing one or more exons adjacent to exon 43 or 53, respectively, in human dystrophin mRNA, wherein said change is due to deletion of one or more nucleotides from the normal nucleotide sequence for said exons, wherein the net of said change in number of the nucleotides is expressed as a reduction of (3×N+1) nucleotides, wherein N is zero or a natural number. The antisense oligonucleotide comprising a nucleotide sequence complementary to the nucleotide sequence set forth under SEQ ID NO:1 may be selected from the group consisting of a DNA having the nucleotide sequence set forth under SEQ ID NO:3 in the Sequence Listing and a phosphorothioate DNA having the same nucleotide sequence as the nucleotide sequence set forth under SEQ ID NO:3, and the antisense oligonucleotide comprising a nucleotide sequence complementary to the nucleotide sequence set forth under SEQ ID NO:2 may be selected from the group consisting of a DNA having the nucleotide sequence set forth under SEQ ID NO:4 in the Sequence Listing and a phosphorothioate DNA having the same nucleotide sequence as the nucleotide sequence set forth under SEQ ID NO:4.

DETAILED DESCRIPTION OF THE INVENTION

In the present invention, "oligonucleotide" includes not only oligoDNA and oligoRNA but also a phosphorothioate analogue such as phosphorothioate oligoDNA. Phosphorothioate DNAs are nucleotides in which an oxygen atom in the phosphate group is replaced with a sulfur atom. They are nucleotide analogues more resistant to various nucleotide decomposing enzymes and therefore widely used in the field of genetic engineering, e.g., for site specific substitution in genes. The method of their production, their properties and their various application are well known to those skilled in the art. Phosphorothioate DNAs, which form base pairs as natural DNAs do, are employed in the present invention with particular advantage as they are more resistant to various decomposing enzymes. "Phosphorothioate analogue" herein is of a structure in which one or more phosphorodiester groups between the nucleotides in a DNA chain are replaced with phosphorothioate groups.

The medicament of the present invention preferably contains 0.05–5 μmol/ml of one of the antisense oligonucleotides, 0.02–10 w/v % of at least one carbohydrate or polyalcohol, and 0.01–0.4 w/v % of at least one pharmaceutically acceptable surfactant. A more preferred concentration range for the antisense oligonucleotide is 0.1–1 μmol/ml.

For the above carbohydrate, monosaccharide and/or disaccharide are preferred. Examples of the carbohydrates and polyalcohols include glucose, galactose, mannose, lactose, maltose, mannitol, and sorbitol. They may be employed alone or in combination.

Examples of preferred surfactants include polyoxyethylene sorbitan mono- to tri-ester, alkyl phenyl polyoxyethylene, sodium taurocholate, sodium cholate, and polyalcohol esters. A particularly preferred one of them is polyoxyethylene sorbitan mono- to tri-ester, and particularly preferred esters are oleate, laurate, stearate, and palmitate. They may be employed alone or in combination.

The medicament of the present invention preferably further contains 0.03–0.09 M of at least one pharmaceutically acceptable neutral salt, for example, sodium chloride, potassium chloride, and/or calcium chloride.

The medicament of the present invention preferably may further contain 0.002–0.05 M of a pharmaceutically acceptable buffering agent. Examples of preferable buffering agents include sodium citrate, sodium glycinate, sodium phosphate, and tris(hydroxymethyl)aminomethane. The buffering agents may be employed alone or in combination.

The above medicaments may be supplied in liquid forms. Considering, however, for cases in which they have to be stored for certain periods of time, it generally is preferred that they are provided in a lyophilized form of composition, in order to stabilize the antisense oligonucleotide and thereby preventing reduction of its therapeutic effect. Prior to use, such a composition is reconstituted, i.e., turned back into a liquid form to be injected, using a solvent (e.g., injectable distilled water). Therefore the medicaments of the present invention include those provided in lyophilized form which are intended to be reconstituted prior to use with a solvent in order to make the concentrations of their ingredients fall within predetermined ranges. For greater stability of such lyophilized compositions, albumin or amino acids such as glycine may be added.

EXPERIMENTS

The present invention will be described in further detail below with reference to the following experiments.

1. Induction of Exon Skipping in Lymphoblastoid Cells Derived from a Patient.

As aforementioned, it was confirmed that the antisense oligonucleotide designed by the present inventor efficiently induced skipping of exon 19 in the splicing reaction on the pre-mRNA transcribed from the dystrophin gene with normal structure. On the other hand, it is expected that the dystrophin pre-mRNA of a DMD patient with deleted exon 20 had abnormal secondary or tertiary structure, since its gene structure is different from the normal one. Thus, study was made to examine whether the above-mentioned 31-base antisense oligonucleotide would work effectively in such a DMD patient. Briefly, as will be described in detail below, EB virus-transformed lymphoblastoid cell lines were established from two DMD patients who lacked dystrophin exon 20. Using these cell lines it was confirmed that the antisense oligonucleotide can induce exon skipping.

(a) Establishment of Lymphoblastoid Cell Lines from DMD Patients

EB virus-transformed lymphoblastoid cell lines were established as follows from two DMD patients who lacked dystrophin exon 20: Two ml of whole blood taken from each of the patients was mixed with 2 ml of RPMI1640 medium (supplemented with 10% FBS) and loaded onto 3 ml of Ficoll Paque (Pharmacia) and then subjected to density-gradient centrifugation. Then, the lymphocyte layer was selectively collected, washed twice with RPMI1640 medium (supplemented with 10% FBS), and suspended in 0.5 ml of RPMI1640 medium (supplemented with 10% FBS) to give a lymphocyte suspension. This suspension was mixed with a 0.5 ml EB virus solution which had been prepared beforehand, and the mixture was cultured at 37° C. for a week. A week later, the culture was washed with RPMI1640 medium (supplemented with 10% FBS) in order to remove the EB virus, and culture was continued with the same medium. Thus, the lymphocytes from the patients were infected with EB virus and gave morphologically large, lymphoblastoid cells.

(b) Incorporation of an Antisense Oligonucleotide

The above obtained culture of lymphoblastoid cell lines were centrifuged to separate cellular component. The cells were cultured at 36° C. for 5 hrs in a maintenance medium containing about 200 nM (200 pmol/ml) of an antisense oligoDNA consisting of a 31-nucleotides sequence complementary to the nucleotide sequence set forth under SEQ ID NO:2 in the Sequence Listing and 2% fetal bovine serum (FBS). The medium then was replaced with a serum medium and culture was continued for additional 12 hrs. After the culture, the cells were collected and the whole RNAs extracted in a conventional manner.

(c) Analysis of Dystrophin cDNA

Using thus obtained whole RNAs as templates, cDNA were synthesized in a conventional manner by reverse transcriptase with random oligonucleotide primers consisting of hexaoligonucleotides. Using thus obtained cDNAs, a region covering dystrophin exon 18 through exon 21 was amplified by nested PCR. The first cycle of amplification was carried out using primers designed for exon 18 and exon 21. Using this amplification product as a template, the second PCR was carried out with primers designed to match to inner regions of those designed for the first primers. This amplification was done with the annealing temperature set at 60° C.

(d) Confirmation of Exon 19 Skipping

The amplification of the region covering from exon 18 through exon 21 of dystrophin cDNA performed without addition of the antisense oligonucleotide gave a clear band of 384 base pairs. Sequencing of this amplification product in a conventional manner confirmed that it consisted of exons 18, 19 and 21. This was in consistent with the result of genetic analysis done on the patient.

On the other hand, using cDNA prepared from the cells which had been treated with the antisense oligoDNA, a smaller-sized amplification product with intact reading frame was also obtained since the fourth day of culture together with an amplification product with the same size as one obtained from the cells in which no antisense oligoDNA was incorporated. By the same method, the lymphoblastoid cells established from the case 2 also gave two types of bands. Sequencing of the smaller-sized ones of these amplification products revealed that exon 18 sequence was connected directly to that of exon 21, with exons 19 and 20 both deleted. This indicates that the treatment with the antisense oligonucleotide caused skipping of exon 19. On the other hand, lymphoblastoid cells established from a normal donor gave only a smaller-sized amplification product in which exon 19 only was skipped. Examination performed on the whole dystrophin cDNA amplified in 10 antibody regions revealed no fragment suggesting further abnormality in splicing.

(e) Discussion

The observed difference in the exon skipping-inducing effect of the antisense oligonucleotide between the normal subject and the DMD patient seemed to be attributable to a difference in the secondary or tertiary structure at or around exon 19 of the pre-mRNA. Efficiency of exon skipping induction was further determined for the DMD patients by applying the antisense oligonucleotide at different concentrations. However, no condition was found under which all the transcript underwent exon skipping as shown in the cells derived from the normal subject. This induction observed with the antisense oligonucleotide was not observed with a sense oligonucleotide or with an antisense oligonucleotides against other regions.

These results indicate that it is possible to correct the reading frame of dystrophin pre-mRNA by inducing an exon skipping through manipulation of its splicing process. It was still unknown, however, whether a mRNA with amino acid reading frame restored by such correction could efficiently synthesize the protein also in muscular cells.

2. Expression of Dystrophin-like Protein in Muscular Cells from DMD Patient

Then, examination was conducted on whether a dystrophin-like protein would be expressed in myoblasts from a DMD patient who lacked exon 20.

(a) Establishment of a Muscular Cell Line from DMD Patient

A specimen of muscular tissue was aseptically taken from a patient who lacked exon 20 in dystrophin gene. The tissue was minced and trypsinized to give dissociated cells. The cells were washed and then cultured in a growth medium (Ham-F10 supplemented with 20% FCS and 0.5% chicken embryo extract). For subcultivation, the muscular cells were cultured on cover slips placed in culture dishes. When the proportion of myoblasts reached about 80%, the medium was replaced with Fusion medium (DMEM supplemented with 2% HS) to induce differentiation into muscular cells.

(b) Incorporation of Antisense OligoDNA

On the fourth day of induction of differentiation, antisense oligoDNA (200 pmol) was introduced into the cells using LipofectAMINE (6 μl), and further cultured for 3, 7 and 10 days.

(c) Immunohistochemical Staining of Dystrophin

After respective incubations, the cells were subjected to immunohistochemical staining using an antibody against the C-terminus of dystrophin. As a result, it was found that dystrophin staining turned positive in the cells in which no dystrophin staining had been detected initially. Dystrophin positive cells were found in any of the cultures. In addition, staining with an antibody against the N-terminal region of dystrophin also gave a similar result to that obtained with the C-terminal staining, thus confirming that the produced dystrophin extended from the N-terminus to the C-terminus.

While dystrophin staining was thus positive in the myoblasts treated with the antisense oligoDNA, no dystrophin staining was observed in myoblasts treated likewise but without addition of the antisense oligoDNA.

(d) Analysis of Dystrophin cDNA

Then, RNA was extracted by a conventional method from the above myoblasts cultured with the antisense oligoDNA. After the synthesis of cDNA from the RNA thus obtained, a region covering dystrophin exons 18–21 was amplified as described above regarding the RNA from lymphoblastoid cells.

The amplification product was then sequenced by a conventional method. As a result, it was found that the in-frame amplification product emerged since the fourth day of culture, in which amino acids reading frame was restored by a direct connection of the exon 18 sequence to that of exon 21.

Then the entire region of the cDNA prepared from the myoblasts cultured with the antisense. oligoDNA was amplified by PCR separately in 10 different portions. The amplified fragments were electrophoresed to determine their sizes by a conventional method. As a result, there were found no fragments suggesting abnormal splicing except for the skipping of exons 19 and 20. These results indicate that the obtained dystrophin mature mRNA was a reading frame-restored, full length mRNA except for the entire loss of exons 19 and 20.

3. Transfer of Antisense OligoDNA into the Nucleus

Then, in order to obtain supportive evidence that the antisense oligoDNA had actually entered the nucleus and worked there, a fluorescence-labeled antisense oligoDNA was employed and its transfer into the nucleus was monitored.

The antisense oligoDNA used above was labeled with FITC (fluorescein isothiocyanate) by a conventional method, and its transfer into the nucleus was examined. Briefly, muscular cells from a DMD patient was cultured in a growth medium (Ham-F10 supplemented with 20% FCS and 0.5% chicken embryo extract). The culture was performed on cover slips placed in culture dishes. When the cells became semiconfluent, the medium was replaced with Fusion medium (DMEM supplemented with 2% HS) to induce differentiation into the muscular cells. On the fourth day of induction of differentiation, the FITC-labeled antisense oligoDNA (200 pmol) was introduced into the cells using LipofectAMINE (6 µl), and 1, 2, 3, 7 and 10 days later, localization of FITC was assessed.

As a result, fluorescence signals localized in the nucleus were detected.

This supports that the antisense oligoDNA entered the nucleus and caused skipping of exon 19 splicing.

As demonstrated by the above results of the experiment, synthesis of a protein corresponding to dystrophin is made possible in the myoblasts of a DMD patient by restoring the amino acids reading frame into in-frame position. This indicates that it is possible to convert patients of DMD, a very serious and so far incurable disease, and in particular those with simple loss of exon 20, to milder BMD patients.

4. Detection of SES in Other Exons

Based on the above results, the present inventor examined exons consisting of odd number of nucleotides relative to a reading frame (therefore, loss of one of such exons would result in an out-of-frame arrangement in reading of amino acids) in and around exons 45–55, the region in dystrophin gene where high incidence of mutation is noted, for sequences which will give rise to SES's as transcripts. According to in vitro analysis, as aforementioned, SES is rich in purine nucleotides (in particular, repeats of sequence "aag"). Based on this, the present inventors selected following three regions as candidates which could provide templates for transcripts relatively rich in purine nucleotides, and examined whether the sequences could give transcripts having SES activity: (1) a 26-nucleotide sequence (nucleotide sequence complementary to the nucleotide sequence set forth under SEQ ID NO:1) within exon 43, (2) a 28-nucleotide sequence within exon 46, and (3) a 26-nucleotide sequence (nucleotide sequence complementary to the nucleotide sequence set forth under SEQ ID NO:2) within exon 53.

For preparation of pre-mRNAs for SES activity assessment, the plasmid described by Watakabe, A. et al., *Genes & Development*, 7:407–418(1993) was employed as the standard plasmid, which included exon 3, intron 3, and a 5'-terminal region of exon 4 of Drosophila doublesex gene (dsx). This was a plasmid prepared by inserting into the BglII-SmaI site of plasmid pSP72 a BglII-HincII fragment from pSPdsxE34f [Inoue et al., *Proc. Natl. Acad. Sci. USA*, 89:8092–8096(1992)], which in turn was a plasmid prepared by subcloning into pSP73 (Promega) a genomic dsx fragment spanning from exon 3 to the site 1128 bp downstream of the female-specific acceptor site of Drosophila doublesex gene (dsx). The BglII-HincII fragment provides a system which allows no splicing between exons on both ends of intron 3 in the transcript when no SES is added immediately downstream of the 5'-terminal region of exon 4, the female-specific exon, but allows splicing when an SES is added there.

For each of nucleotide sequences to be evaluated, single stranded, forward and reverse DNAs were synthesized separately. A BamHI cleaving site was added to the forward DNAs at their 5'-terminus. A XhoI cleaving site was added to the reverse DNAs at their 5'-terminus. The forward and reverse DNAs thus prepared were combined, heated (94° C., 2 min), and annealed at room temperature to obtain a double stranded DNA. The double stranded DNA was inserted into the BamHI-XhoI site located immediately downstream of the 5'-terminal region of dsx exon 4 in the standard plasmid for assessment described above. Thus, plasmids were obtained each of which included a mini-gene consisting of nucleotide sequence spanning from exon 3 to 5'-terminal region of exon 4 of dsx and a nucleotide sequence to be evaluated.

Radio isotope-labeled pre-mRNAs were prepared in a conventional manner with RNA polymerase using these plasmids as templates. These pre-mRNA then were reacted with a HeLa cell nucleus extract for 1 hr in the same manner as aforementioned to allow splicing to proceed, and the products were analyzed by gel electrophoresis in a conventional manner.

As a result, splicing reaction on a pre-mRNA in which one of the SES candidates from 43 or 53 was incorporated clearly gave rise to the mRNA which underwent splicing at intron 3. This indicates that these two SES candidate sequences actually have SES activity. Between the two, SES activity was stronger with the candidate from exon 43. On the other hand, although the splicing reaction using pre-mRNA in which the SES candidate from exon 46 was incorporated gave the spliced mRNA, its activity proved to be very weak.

Thus, the present inventors found that SES's are present within exons 43 and 53 of human dystrophin mRNA. Those SES's are the ribonucleotide sequences set forth under SEQ ID NO:1 and NO:2.

It has already been found by the present inventors that an SES is present in exon 19 of transcript pre-mRNA of dystrophin gene and that skipping of exon 19 can be induced by means of an antisense oligonucleotide against the SES, thereby restoring the reading frame. With regard to the additional SES's identified above within exons 43 and 53, respectively, their antisense oligonucleotides when applied are expected to induce skipping of exon 43 (173 nucleotides, i.e., 3×57+2 nucleotides) and exon 53 (212 nucleotides, i.e., 3×70+2 nucleotides), respectively.

For a DMD case which is characterized by a reduction of (3×N+1) nucleotides (N is zero or a natural number) due to a loss of nucleotides in one or more exons adjacent to exon 43 of dystrophin pre-mRNA, therefore, skipping of exon 43 during splicing will be induced by administering an antisense oligonucleotide against the SES within exon 43. By so doing, it is possible to correct the out-of-frame mutation, restoring an in-frame structure, for the further loss of 173 nucleotides in exon 43 through splicing will make the total number of lost nucleotides in the spliced mRNA to be a multiple of 3. Thus, although the amino acids corresponding to the skipped nucleotide sequence will be lost, downstream amino acid sequence will become unaffected by the abnormality of the gene, and a dystrophin will thus be synthesized, converting serious DMD to milder BMD. Examples of such DMD cases include those with the loss of exon 44 (148 nucleotides, i.e., 3×49+1 nucleotides), of exons 44 to 46 (148+176+148=472 nucleotides, i.e.,3×157+1 nucleotides), of exons 44 to 47 (148+176+148+150=622 nucleotides, i.e., 3×207+1 nucleotides), of exons 44 to 48 (148+176+148+ 150+186=808 nucleotides, i.e., 3×269+1 nucleotides), or of exons 44 to 49 (148+176+148+150+186+102=910 nucleotides, i.e., 3×303+1 nucleotides).

Similarly, for a DMD case which is characterized by a reduction of (3×N+1) nucleotides (N is zero or a natural number) due to a loss of nucleotides in one or more exons adjacent to exon 53 of dystrophin pre-mRNA, therefore, skipping of exon 53 during splicing will be induced by administering an antisense oligonucleotide against the SES within exon 53. Examples of such cases include DMD cases with the loss of exon 52 (118 nucleotides, i.e., 3×39+1 nucleotides), of exons 50, 51 and 52 (109+233+118=460 nucleotides, i.e., 3×153+1 nucleotides). For these cases, by inducing exon 53 skipping during splicing through introduction of antisense oligonucleotide against the SES in exon 53, it is possible to modify the number of deleted nucleotides in the spliced mRNA into 330 and 672, respectively. By so doing, the number of deleted nucleotides in the spliced mRNA will become a multiple of 3 and therefore the existing shift of the reading frame due to the original deletion will be corrected.

Administration of an antisense oligonucleotide of the present invention to a corresponding DMD patient can be made as follows. For example: according to the type of a given case, an antisense oligoDNA comprising a nucleotide sequence complementary to the nucleotide sequence set forth under SEQ ID NO:1 or NO:2, e.g., the antisense oligoDNA set forth under SEQ ID NO:3 or NO:4 in the Sequence Listing, or an antisense phosphorothioate oligoDNA having the same nucleotide sequence, produced by a conventional method well known to those skilled in the art is sterilized by a conventional method and formed into, for example, a 1200 μg/ml injectable solution. The solution is then intravenously administered to a patient, for example by dropwise infusion of a parenteral fluid, at a dose of, for example, 20 mg of the antisense oligonucleotide per kg body weight. The administration is made four time at two-week intervals, for example. Later administration is repeated as needed while monitoring expression of the dystrophin protein in muscle tissue biopsy samples, serum creatine kinase levels, and therapeutic effect assessed on the basis of clinical symptoms. As far as it takes effect without apparent side effect, the therapy is generally continued over the patient's life.

COMPOSITION EXAMPLES

The present invention is described in further detain with reference to some representative composition examples blow. It is not intended, however, that the scope of the present invention be restricted by the composition examples. <Preparation of Antisense OligoDNA and Phosphorothioate OligoDNA>

DNAs and phosphorothioate oligoDNAs having a nucleotide sequence complementary to the nucleotide sequence set forth under SEQ ID NO:1 or NO:2 in the Sequence Listing may be produced using a commercially available DNA synthesizer such as Applied Biosystems Model 1380B, and according to the method described in Zon et al., [Oligonucleotides and Analogues: A Practical Approach, F. Eckstein, Ed., p.87–108, Oxford University Press, Oxford, England; U.S. Pat. No. 5,151,510].

COMPOSITION EXAMPLE 1

According to the following formula, necessary amount of respective base components are admixed to dissolve. The antisense oligonucleotide then is dissolved in the solution, the solution is made to volume and filtered through a membrane filter with a pore size of 0.22 μm to obtain a composition for intravenous administration. Antisense oligonucleotide (*1) - - - 500 mg Sodium chloride - - - 8.6 g Potassium chloride - - - 0.3 g Calcium chloride - - - 0.33 g Distilled water for injection - - - to 1000 ml *1: phosphorothioate oligoDNA consisting of a nucleotide sequence set forth under SEQ ID NO:3 in the Sequence Listing

COMPOSITION EXAMPLE 2

According to the following formula, necessary amount of respective base components are admixed to dissolve. The antisense oligonucleotide then is dissolved in the solution, the solution is made to volume and filtered through a filter with a pore size of 15 nm (PLANOVE 15: Asahi Chemical Industry Co., Ltd.) to obtain a composition for intravenous administration. Antisense oligonucleotide (*2) - - - 100 mg Sodium chloride - - - 8.3 g Potassium chloride - - - 0.3 g Calcium chloride - - - 0.33 g Sodium hydrogen phosphate.12H$_2$O - - - 1.8 g 1N hydrochloric acid - - - q.s. (pH 7.4) Distilled water for injection - - - to 1000 ml *2: phosphorothioate oligoDNA consisting of a nucleotide sequence set forth under SEQ ID NO:4 in the Sequence Listing

COMPOSITION EXAMPLE 3

According to the following formula, necessary amount of respective base components are admixed to dissolve. The antisense oligonucleotide then is dissolved in the solution, the solution is made to volume and filtered through a filter with a pore size of 35 nm (PLANOVE 35: Asahi Chemical Industry Co., Ltd.) to obtain a composition for intravenous administration. Antisense oligonucleotide (*3) - - - 100 mg Sodium chloride - - - 8.3 g Potassium chloride - - - 0.3 g Calcium chloride - - - 0.33 g Glucose - - - 0.4 g Sodium hydrogen phosphate.12H$_2$O - - - 1.8 g 1N hydrochloric acid - - - q.s. (pH 7.4) Injectable distilled water - - - to 1000 ml *3: phosphorothioate oligoDNA consisting of a nucleotide sequence set forth under SEQ ID NO:3 in the Sequence Listing

What is claimed is:

1. An oligonucleotide selected from:

an RNA consisting of the nucleotide sequence set forth as SEQ ID NO: 1, or a DNA consisting of the nucleotide sequence set forth as SEQ ID NO: 1 modified such that each uracil nucleotide of SEQ ID NO: 1 is replaced with thymine.

2. An oligonucleotide selected from:

an RNA consisting of the nucleotide sequence set forth as SEQ ID NO: 2, or a DNA consisting of the nucleotide sequence set forth as SEQ ID NO: 2 modified such that each uracil nucleotide of SEQ ID NO: 2 is replaced with thymine.

* * * * *

```
                            SEQUENCE LISTING

<160> NUMBER OF SEQ ID NOS:  6

<210> SEQ ID NO 1
<211> LENGTH: 26
<212> TYPE: RNA
<213> ORGANISM: Homo sapiens

<400> SEQUENCE: 1
agcaagaaga cagcagcauu gcaaag                                        26

<210> SEQ ID NO 2
<211> LENGTH: 26
<212> TYPE: RNA
<213> ORGANISM: Homo sapiens

<400> SEQUENCE: 2
ggaagcuaag gaagaagcug agcagg                                        26

<210> SEQ ID NO 3
<211> LENGTH: 31
<212> TYPE: DNA
<213> ORGANISM: Homo sapiens

<400> SEQUENCE: 3
gcactttgca atgctgctgt cttcttgcta t                                  31

<210> SEQ ID NO 4
<211> LENGTH: 31
<212> TYPE: DNA
<213> ORGANISM: Homo sapiens

<400> SEQUENCE: 4
gacctgctca gcttcttcct tagcttccag c                                  31

<210> SEQ ID NO 5
<211> LENGTH: 16
<212> TYPE: DNA
<213> ORGANISM: Homo sapiens

<400> SEQUENCE: 5
gcaagatgcc agcaga                                                   16

<210> SEQ ID NO 6
<211> LENGTH: 31
<212> TYPE: DNA
<213> ORGANISM: Homo sapiens

<400> SEQUENCE: 6
aactgcaaga tgccagcaga tcagctcagg c                                  31
```